United States Patent
Suh et al.

(10) Patent No.: US 7,479,143 B2
(45) Date of Patent: Jan. 20, 2009

(54) UNIDIRECTIONAL FIXATION DEVICE

(75) Inventors: Sean S Suh, Plymouth Meeting, PA (US); David S Rathbun, Gap, PA (US)

(73) Assignee: Synthes (U.S.A.), West Chester, PA (US)

( * ) Notice: Subject to any disclaimer, the term of this patent is extended or adjusted under 35 U.S.C. 154(b) by 590 days.

(21) Appl. No.: 11/078,802

(22) Filed: Mar. 11, 2005

(65) Prior Publication Data

US 2006/0217724 A1    Sep. 28, 2006

(51) Int. Cl.
*A61B 17/80*  (2006.01)
*A61B 17/70*  (2006.01)
(52) U.S. Cl. .............................. 606/71; 606/280; 606/70
(58) Field of Classification Search ............... 606/61, 606/69–71, 280–71
See application file for complete search history.

(56) References Cited

U.S. PATENT DOCUMENTS

| 3,385,299 | A | * | 5/1968 | Le Roy ................. 606/218 |
| 5,470,333 | A | * | 11/1995 | Ray ...................... 606/61 |
| 5,616,142 | A | * | 4/1997 | Yuan et al. ............. 606/61 |
| 5,964,763 | A |   | 10/1999 | Incavo et al. |
| 6,602,257 | B1 | * | 8/2003 | Thramann ............. 606/69 |
| 2002/0089267 | A1 | * | 7/2002 | Paczkowski et al. ...... 312/72 |
| 2003/0060828 | A1 |   | 3/2003 | Michelson |
| 2003/0130661 | A1 | * | 7/2003 | Osman ................... 606/71 |
| 2004/0019353 | A1 |   | 1/2004 | Fried et al. |
| 2004/0097938 | A1 |   | 5/2004 | Neville |

FOREIGN PATENT DOCUMENTS

DE   26 21 175     11/1977
GB   2208476 A  *  4/1989

* cited by examiner

*Primary Examiner*—Eduardo C Robert
*Assistant Examiner*—Julianna N Harvey
(74) *Attorney, Agent, or Firm*—Stroock & Stroock & Lavan LLP

(57) ABSTRACT

A fixation system may comprise at least one carriage element being capable of receiving one or more bone fasteners. The carriage element is mountable on a plate, and the plate has an engaging portion for adjustably securing the carriage element to the main plate. The engaging portion of the carriage element allows translational movement of the carriage plate with respect to the plate in only one axial direction. In one embodiment, the plate includes arms for receiving the carriage element and the carriage element includes channels mountable on the arms, with the engaging portion disposed within the channels.

8 Claims, 8 Drawing Sheets

UNIDIRECTIONAL FIXATION DEVICE

FIELD OF THE INVENTION

This invention relates to the field of fixation devices. More particularly, this invention relates to a fixation system for spines, the fixation system being capable of unidirectional translational adjustment.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also acts to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer the endplates, increasing the chances that fusion will occur. Often in the period immediately following surgery, the spacer will subside slightly either into the under-portion of the endplates or due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited translation of the vertebrae with respect to at least a portion of the plate, thereby limiting the undesirable effects of load shielding by the plate due to graft subsidence caused by settling or normal forces experienced in the spinal column. Promoting fusion of the adjacent vertebrae is thus accomplished.

However, fasteners used with both rigid and translational plates have a tendency to back-out of their installed positions under the influence of force and movements of the spine. The back-out of the fasteners is undesirable, as the fixation assembly may shift post-operatively to an undesired location, or loosen to an undesirable level.

Therefore, there exists a need for a fixation system that provides stability and promotes fusion while preventing graft movement and enabling compression of the graft. There also exists a need for a fixation system that allows for continued post-operative compression of bone segments. There further exists a need for a fixation system that adjusts only in the direction of increased compression.

SUMMARY OF THE INVENTION

In accordance with the invention, a fixation system may comprise at least one carriage element being capable of receiving one or more bone fasteners, the carriage element being mountable on a plate, and a securing element for adjustably securing the carriage element to the plate, the securing element allowing translational movement of the carriage plate with respect to the plate in only one axial direction. In one embodiment, the plate includes arms for receiving the carriage element and the carriage element includes channels mountable on the arms, with the securing element disposed within each channel. The arms can include an engaging portion that engages with the securing element, the engaging portion comprising a series of ridges that can engage the securing element. In a preferred embodiment, the engaging portion and securing element are in the form of a ratchet and pawl construction.

A fixation system is described that may comprise a first carriage element capable of receiving one or more bone fasteners, and may have a first channel with a least one securing element disposed therein; a first plate may have a first arm insertable in a channel; wherein the first arm has a first engaging portion, the first engaging portion may have a series of ridges configured to engage a securing element; and wherein the first carriage element may be configured to axially translate in only one direction relative to the first plate.

The first carriage element may be allowed to translate in situ. The first plate may have a second arm having a second engaging portion insertable into the first carriage element. The first channel may have a groove configured to receive a portion of a securing element. The securing element may be an engaging clip.

The fixation system may further comprise a second carriage element. The first carriage element may be configured to be associated with a first bone segment, and the second carriage element may be configured to be associated with a second bone segment. The first and second bone segments may be adjacent vertebrae.

The securing element may be configured to expand and retract during translation. The ridges may be configured to provide progressive resistance.

The first carriage element may have at least one fastener hole for receiving a bone fastener. The first plate may have a body section having a longitudinal axis, and the first arm may extend substantially transverse to the longitudinal axis of the body section. The fixation system may further comprise a second plate. The first plate and first carriage element may be curved to accommodate a desired body site.

A method for fixating a plurality of bone segments is also described, comprising the steps of: (a) providing a fixation system comprising: first and second carriage elements capable of receiving one or more bone fasteners, and each having a channel with a least one securing element disposed therein; a first plate having arms insertable in a channel; wherein each arm has a first engaging portion, the first engaging portion having a series of ridges configured to engage a securing element; (b) positioning the assembly adjacent to a desired body site; (c) attaching the first carriage element to a first bone segment with at least one bone fastener, and the second carriage element to a second bone segment with at least one fastener; and (d) allowing the system to translate in situ.

The method may further comprise the step of manually compressing the fixation system. The system may be configured to axially translate in only one direction. The system may be configured to translate incrementally.

A fixation system kit is also described comprising a plurality of carriage elements capable of receiving one or more bone fasteners, each having a first channel with a least one securing element disposed therein; at least one plate having arms insertable in a channel; wherein each arm has a first engaging portion, the first engaging portion having a series of ridges configured to engage a securing element; and wherein at least two of the carriage elements are of a substantially different size. The kit may further comprise at least one bone fastener.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE INVENTION

The system described herein may be used in spinal fusion procedures in which a damaged or diseased disc (or part of a disc) is removed from between a pair of vertebrae and a spinal fusion spacer is placed between the vertebrae. The carriage elements may be applied to an anterior portion of the affected vertebrae to span the affected disc space, and may be fixed to the vertebrae using bone fasteners. The system may function to maintain the vertebrae aligned during the initial period following fixation in which fusion of the spacer to the adjacent vertebrae occurs. The system may also function to share some of the axial spinal load applied to the fusion spacer to prevent extreme subsidence of the spacer into the vertebral body, such as where the patient has poor bone quality. The system may also act to prevent the spacer from being expelled from the disc space during the initial post-operative period.

The system may be used for single level (i.e. one-disc) or multiple-level (i.e. multiple disc) fusion procedures. Some embodiments may be used for corpectomy procedures, in which at least a portion of a vertebral body is removed. Single level systems generally may have two pairs of bone fastener holes, while the multi-level systems generally may have three or more pairs of fastener holes.

Figure 1:
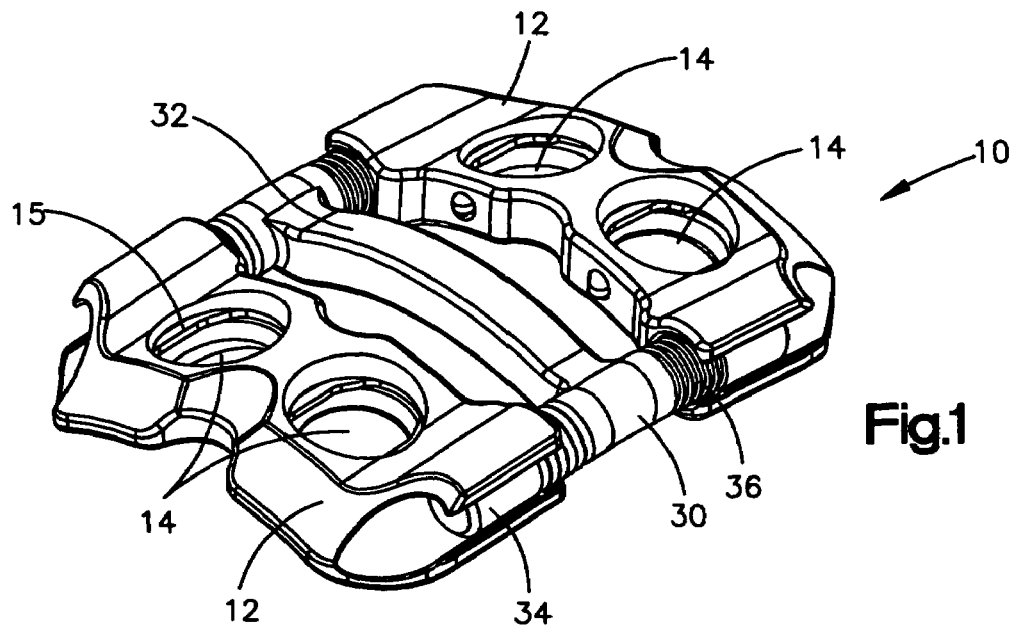
FIG. 1 is a perspective view of an embodiment of the fixation system of the present invention comprising a main plate and two carriage elements.
Figure 2:
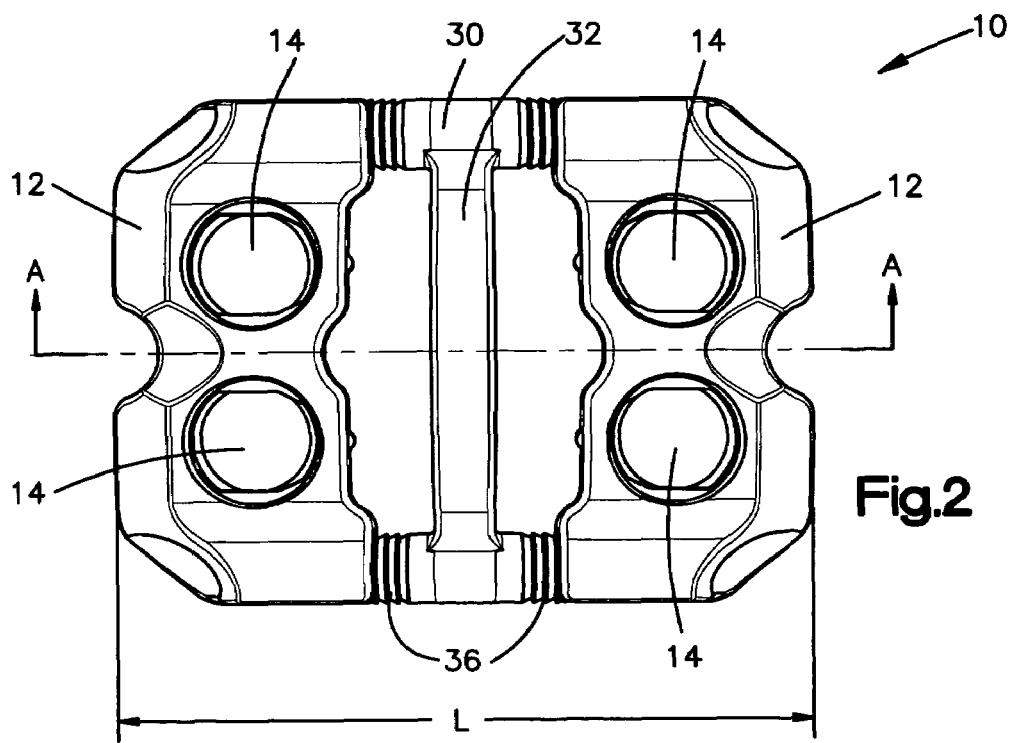
FIG. 2 is a top view of the spinal fixation system of FIG. 1.
Figure 3:
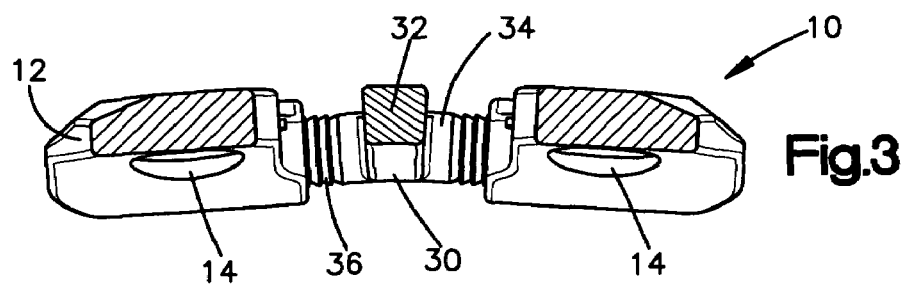
FIG. 3 is a cross-sectional view through line A-A of FIG. 2.

FIG. 1 illustrates a perspective view of one embodiment of a fixation system 10 of the present invention comprising a main plate 30 and two carriage elements 12. The fixation system 10 is shown in top view in FIG. 2, and in side view in FIG. 3. Fixation system 10 may have a longitudinal axis A-A, a length "L," and may comprise at least one carriage element 12, discussed in more detail in relation to FIGS. 4-5, infra. Carriage elements 12 may have at least one fastener hole 14 for receiving at least a portion of a bone fastener (not shown). Fixation system 10 may also comprise of a plate 30, discussed in more detail in relation to FIGS. 6-9B, infra. Plate 30 may have a body portion 32 and at least one arm 34 extending from the body portion 32. Arms 34 may have an engaging portion 36 with ridges 37 for engaging a carriage element 12.

Figure 4:
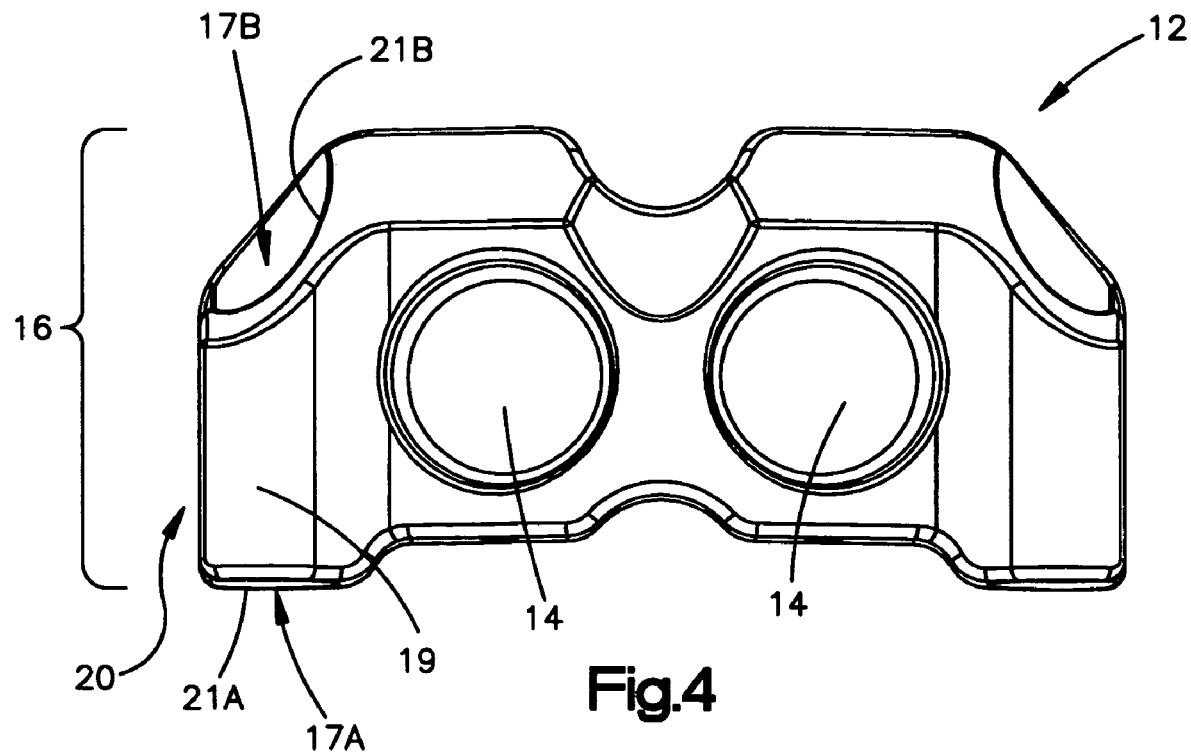
FIG. 4 is a top view of a carriage element of the fixation system of FIG. 1.
Figure 5:
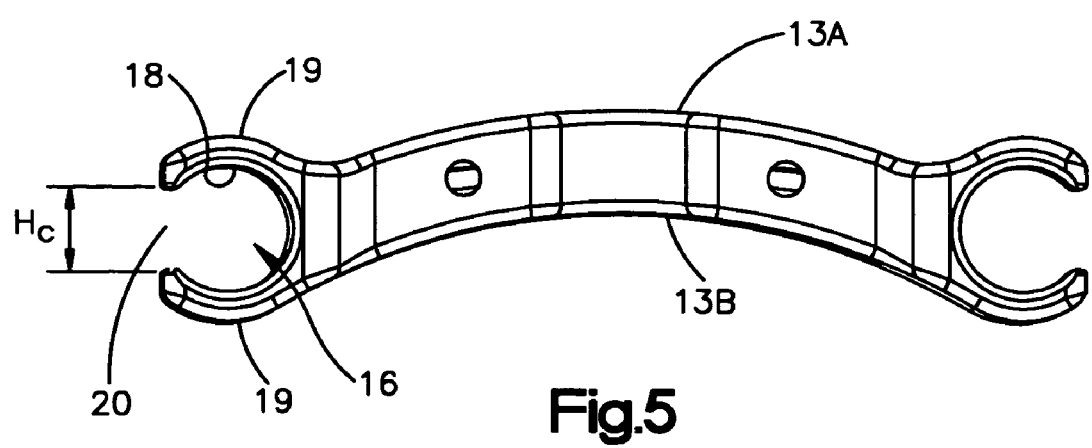
FIG. 5 is a front view of the carriage element shown in FIG. 4.

Referring to FIGS. 4-5, each carriage element 12 may comprise at least one fastener hole 14 for receiving a bone fastener, which may allow the carriage element to be affixed to a bone segment. In the embodiment shown in FIGS. 4-5, each carriage element 12 comprises two fastener holes 14, the bone fasteners being omitted from the illustration for purposes of clarity. However, it is expressly contemplated that a carriage element 12 may have one, three, or more fastener holes 14 as needed or desired. Fastener holes 14 may also be fitted with captive clips 15 to prevent bone fastener back-out, the details, materials, and methods of which are described in U.S. patent application Ser. No. 10/653,164 entitled "Bone Plate with Captive Clips", by Duong, et al., filed Sep. 3, 2003, the entire disclosure of which application is expressly incorporated by reference herein.

Carriage elements 12 may further comprise at least one channel 16 for receiving at least a portion of plate 30, the engagement of which is discussed in more detail below. Channel 16 may have openings 17A, 17B, and extend at least a portion of the way through the body of a carriage element 12. Channel 16 may also have a cutaway portion 20 extending between openings 17A, 17B. Cutaway portion 20 may have a cutaway height $H_c$. Each opening 17A, 17B may be generally circularly shaped to receive a similarly shaped arm 34 of plate 30. Each opening 17A, 17B may also have an edge 21A, 21B. Channel 16 may also have an inner surface 18 and an outer surface 19 of the carriage element 12 disposed opposite the inner surface 18. In the embodiments shown herein, each carriage element 12 has two channels 16, with each channel 16 having two openings 17. However, it is expressly contemplated that a carriage element may have one, three or more channels 16 with an varying number of openings as well. Such variations will be appreciated by those skilled in the art.

Carriage element 12 may also have an upper surface 13A and a lower surface 13B. One or both surfaces 13A, 13B may be generally curved along the length of carriage element 12, as may be seen more clearly in FIG. 5. Such curvature may be advantageous to allow a carriage element 12 to more closely conform to a desired body site or bone segment.

Figure 6:
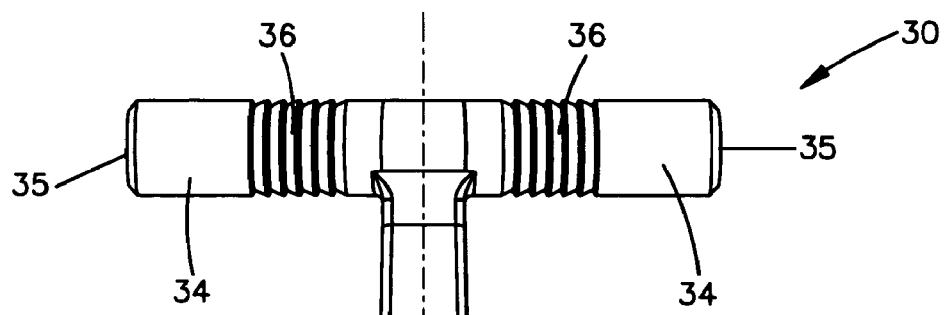
FIG. 6 is a top view of the plate of the fixation system of FIG. 1.
Figure 7:
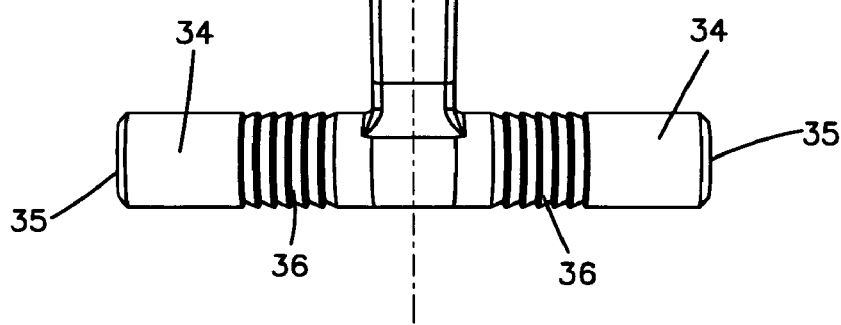
FIG. 7 is a front view of the plate of FIG. 5.
Figure 8:
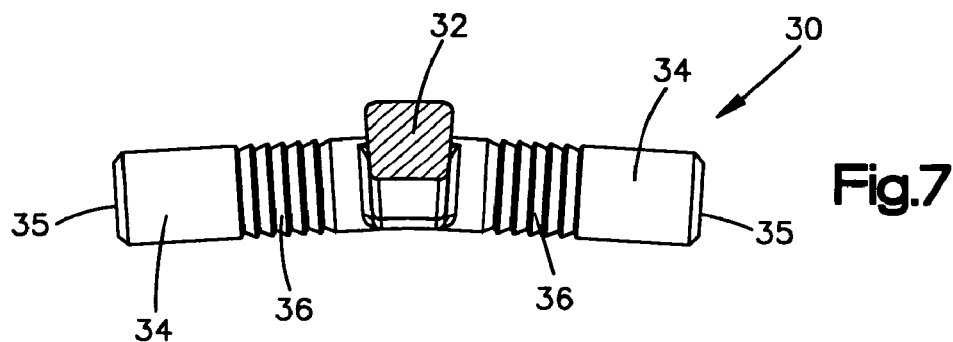
FIG. 8 is a side view of the plate of FIG. 5.
Figure 9A:
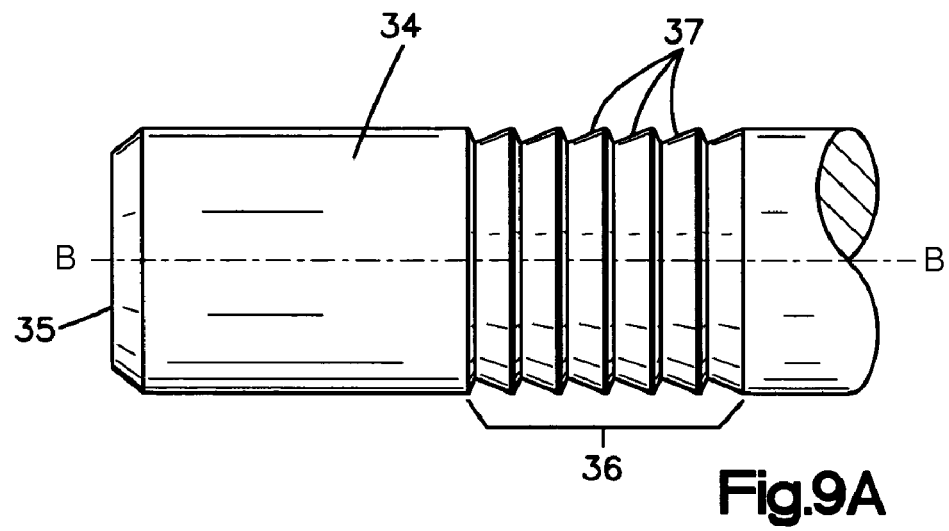
FIG. 9A is an enlarged view of an engaging portion of FIG. 5.
Figure 9B:
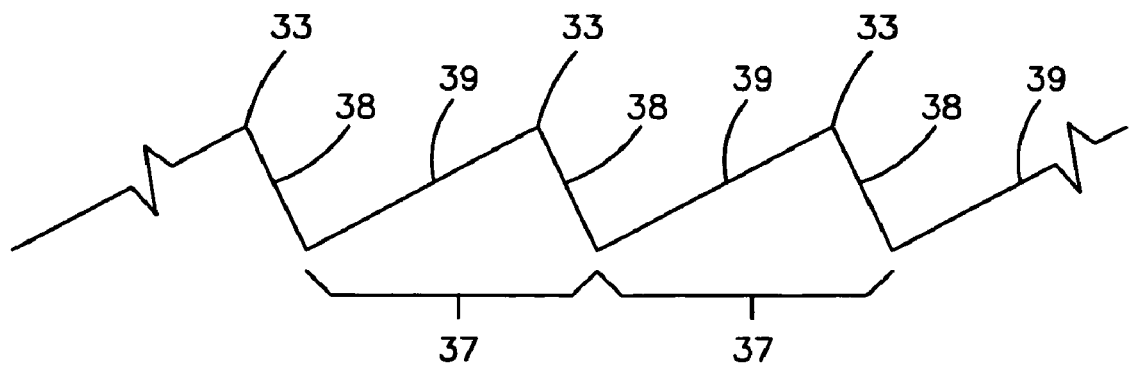
FIG. 9B is an enlarged view of the engaging portion of FIG. 9.

An embodiment of a plate 30 is illustrated in FIGS. 6-9B. A top view of plat 30 is shown in FIG. 6. A front view of plate 30 is shown in FIG. 7. A side view of plate 30 is shown in FIG. 8. Enlarged views of the engaging portion 36 of plate 30 are shown in FIGS. 9A-9B. Main plate 30 may include a body portion 32 and at least one arm 34, and a longitudinal axis B-B. Arms 34 may extend from body portion 32 transversely away from longitudinal axis B-B, and may be sized and dimensioned to be at least partially received within channels 16 of carriage elements 12. Arms 34 may also have ends 35.

Arms 34 may further have an engaging portion 36, which may contain ridges 37. As seen in more detail in FIGS. 9A and 9B, each ridge 37 may include a forward surface 39, a rear surface 38, with an apex 33 disposed therebetween. The forward 39 and rear surfaces 38 may be arranged in an engaging portion 36 such that the surfaces 38, 39 alternate along the length of an engaging portion 36. The resulting engaging portion may therefore have consecutive forward surfaces 39 from one perspective, and consecutive rear surfaces 38 from the opposite perspective.

Ridges 37 within an engaging portion 36 may be substantially the same size, or may be of varying sizes. The size of an engaging portion 36 may vary on different arms 34 of a single plate 30 and/or a single fixation system 10. An arm 34 may have more than one engaging portion 36. Each apex 33 may be in the shape of a point, or may be substantially rounded. For arms 34 of a generally circular cross-section, the maximum cross-sectional diameter of each such arm 34 may be at an apex 33.

Figure 10:
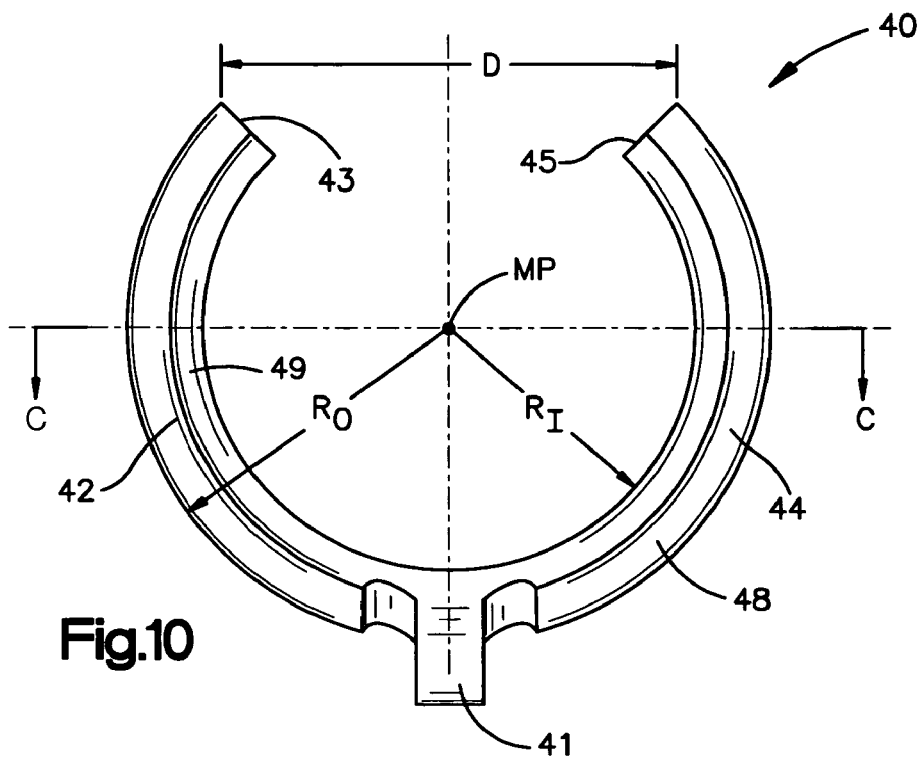
FIG. 10 is a top view of an engaging clip configured to assist in the unidirectional translational motion between a carriage element and the main plate.
Figure 11:
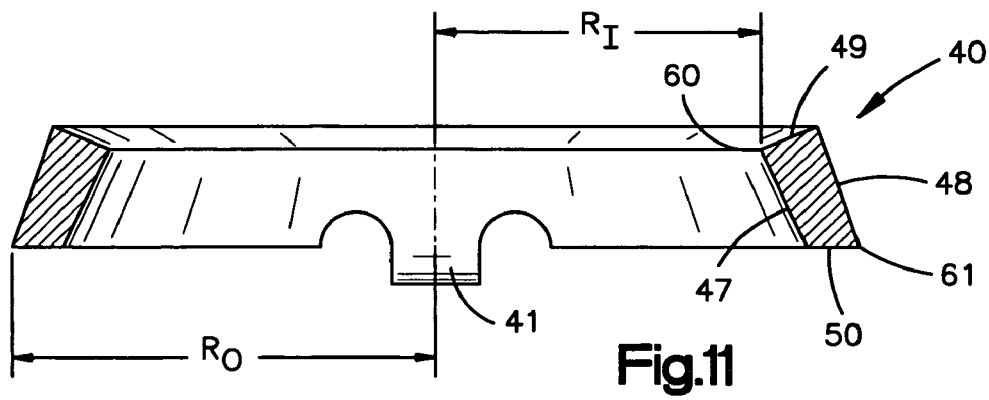
FIG. 11 is a cross-sectional view of the engaging clip of FIG. 10 taken along the line C-C.
Figure 12:
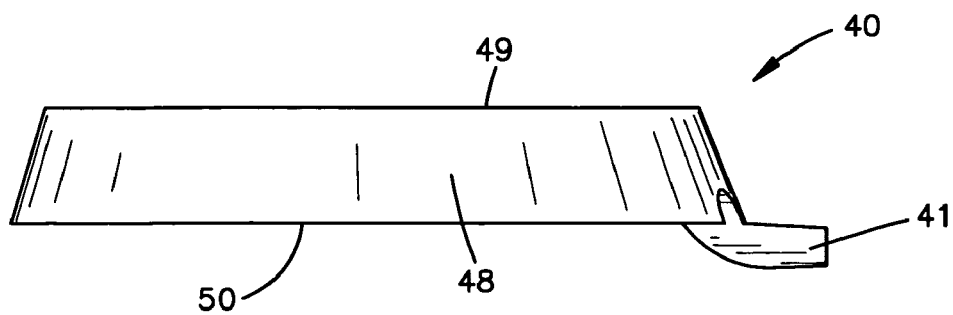
FIG. 12 is a side view of the engaging clip of FIG. 10.

An embodiment of a engaging clip 40 is shown in FIGS. 10-12. A top view is seen in FIG. 10, a cross-sectional view in FIG. 11, and a side view in FIG. 12. Generally, each carriage element 12 may be provided with at least one engaging clip 40 for affecting secure engagement between arms 34 of plate 30 and channels 16 of carriage element 12. In the embodiment illustrated in FIGS. 10-12, engaging clip 40 comprises two arcuate prongs 42, 44 having ends 43, 45 respectively, with a distance "D" between ends 43, 45. Distance D may be substantially the same as cutaway height $H_c$ of cutaway 20 of carriage element 12.

FIG. 11 shows a cross-sectional view of the engaging clip 40 of FIG. 10, taken along the line C-C. As seen in this view, prongs 42 and 44 may have a polygonal cross-sectional shape having four surfaces 47, 48, 49, 50. As described in more detail below, inner surface 47 may engage forward surfaces 39 of ridges 37, and side surface 49 may engage rear surfaces 38 of ridges 37. Moreover, the dimensions of inner surface 47 and side surface 49 may be substantially equivalent to the dimensions of forward surfaces 39 and rear surfaces 38, respectively.

Engaging clip 40 may also have a midpoint MP. Engaging clip 40 may have an inner radius $R_I$ and an outer radius $R_o$. Inner radius $R_I$ may be defined by the distance from the midpoint MP to the edge 60 between inner surface 47 and side surface 49. Outer radius $R_o$ may be defined by the distance from midpoint MP to the edge 61 between outer surface 48 and side surface 50.

Figure 13:
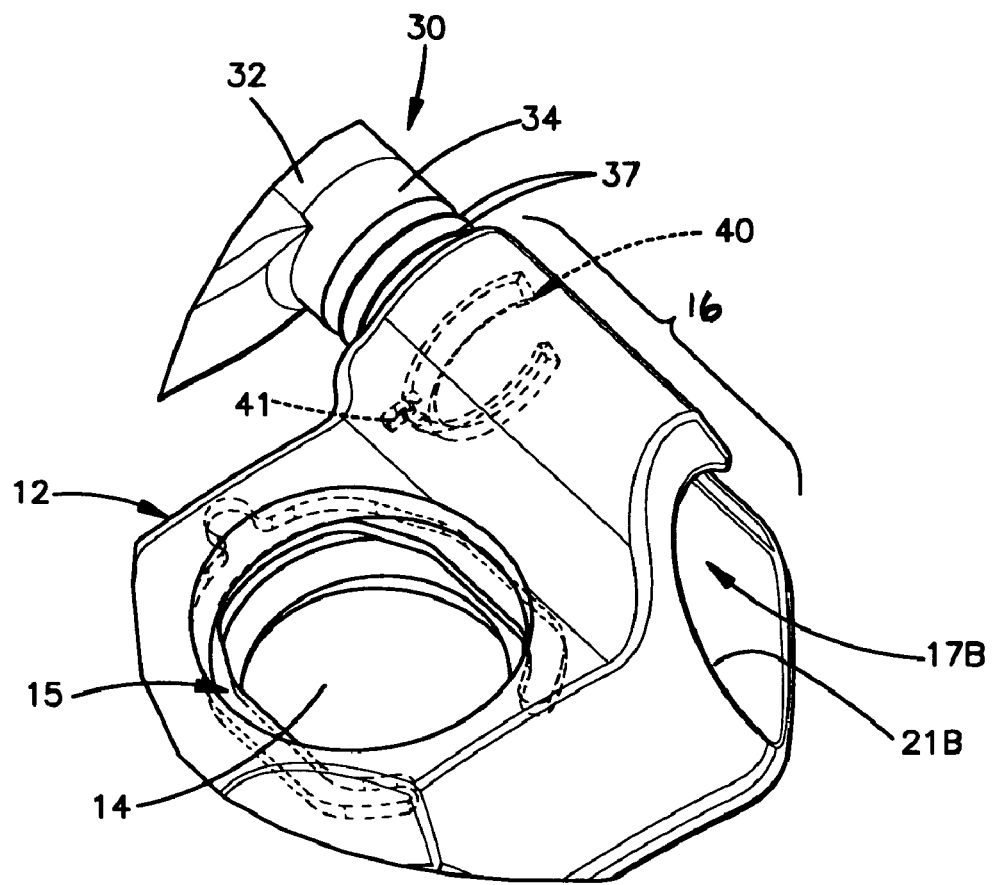
FIG. 13 is a partial perspective view of an engaging clip shown in phantom lines as installed within a carriage element.
Figure 14:
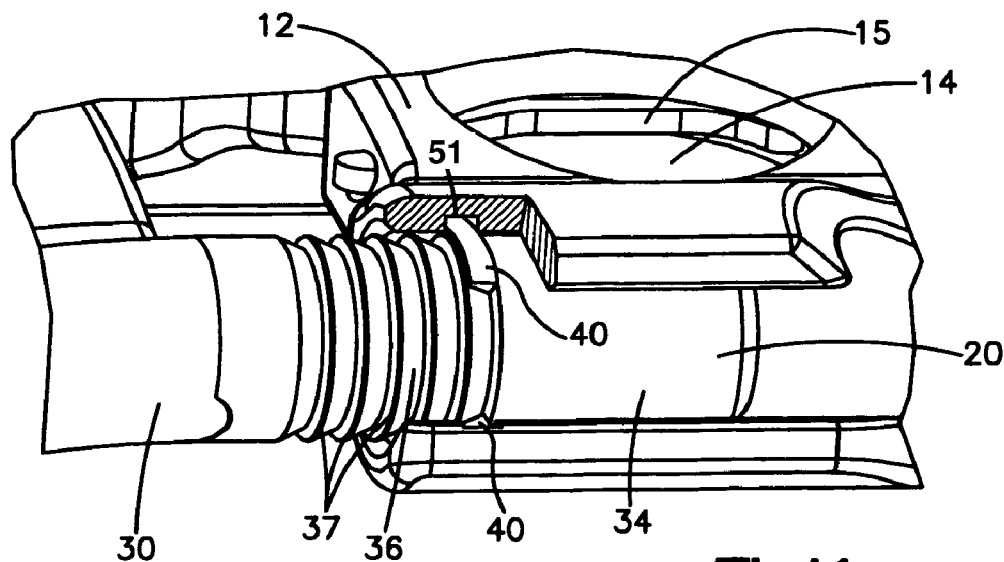
FIG. 14 is partial perspective view of an engaging clip as installed within a carriage element and engaging a main plate.

The engagement of engaging clip 40 to carriage element 12 is shown in FIGS. 13-14, which are partial, enlarged perspective views. As seen in FIG. 13, with carriage element 12 drawn in line form for clarity, an engaging clip 40 may engage carriage element 12 such that the engaging clip 40 is disposed along the inner surface 18 of a channel 16. Channel 16 may have a groove 51 and notch (not shown) disposed along the inner surface 18 for receiving at least a portion of an engaging clip 40. A portion of prongs 42, 44 may be inserted into the groove 51 and retaining element 41 may be inserted into the notch. The result may preferably be that engaging clip 40 is fixedly seated within carriage element 12, and retaining element 41 is inserted into notch to prevent rotation of the engaging clip 40 relative to the carriage element 12. The engagement of engaging clip 40 to carriage element 12 is also shown in FIG. 14, with a portion of the carriage element 12 for clarity.

Generally, at least one carriage element 12 engages a plate 30, specifically at the engaging portion(s) 36 of plate 30. Engaging clip 40 may engage ridges 37 of an engaging portion 36. The ridges 37 may be arranged, and the engaging clip 40 may be dimensioned and sized, such that the clip 40 may only engage sequential ridges 37 in a single direction. The effect of such a relationship is that a carriage element 12 may be allowed to translate unidirectionally relative to a plate 30. By way of example, the carriage element 12 and plate 30 shown in FIG. 14 are engaged in such a way that engaging clip 40 may only engage subsequent ridges 37 to the left of where the clip 40 currently sits. As stated above, this unidirectional relationship may be achieved by sizing the surfaces 38, 39 of ridges 37 and clip prongs 42, 44 of engaging clip 40 so that once an engaging clip 40 translates from a first ridge 37A to a second ridge 37B, the engaging clip may not re-engage the first ridge 37A—the clip 40 may only translate in the other direction via prongs 42, 44. Ridges 37 may also be arranged in a "progressive resistance" format, the details and advantages of which, in addition to details of unidirectional translatable fixation, are described in U.S. patent application Ser. No. 11/001,902 entitled "Unidirectional Translation System for Bone Fixation", by Barrall et al., filed Dec. 1, 2004, the entire disclosure of which application is expressly incorporated by reference herein.

Figure 15A:
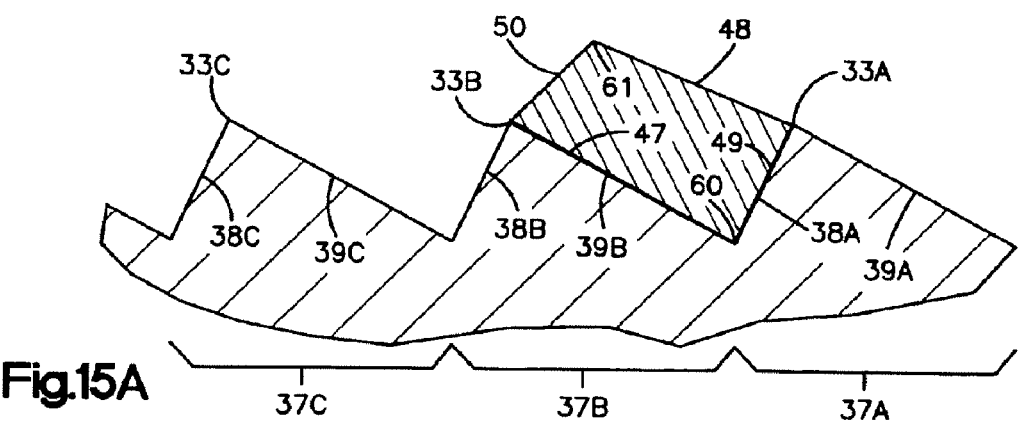
FIGS. 15A-15C are enlarged views of the progression of an engaging clip translating along an engaging portion of a carriage element.
Figure 15B:
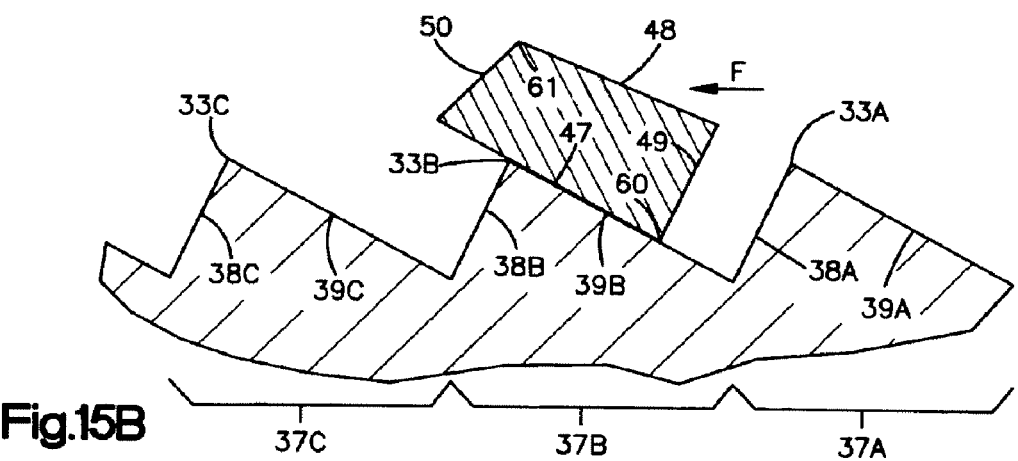
Figure 15C:
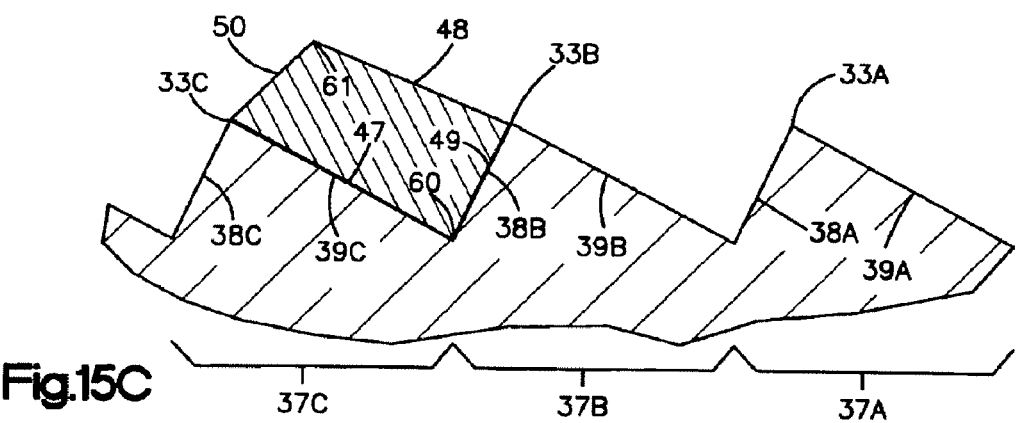

FIGS. 15A-15C show the progression of an engaging clip 40 translating from a first ridge 37A to a second ridge 37B. As shown in FIG. 15A, engaging clip 40 engages ridge 37A, with side surface 49 of clip 40 adjacent rear surface 38A, and inner surface 47 of clip 40 adjacent forward surface 39B. Upon a force "F" acting in the direction as shown, clip 40 may expand and translate in the direction of second ridge 37B. More specifically, the expansion of clip 40 (which may be made of a resilient material, discussed below) may occur in the flexibility of prongs 42, 44 (see FIG. 10), wherein the ends 43, 45 may be pushed outwards and away from midpoint MP. The expansion of clip 40 is shown in FIG. 15B, wherein clip 40, upon the impetus of force F, is translating away from apex 33A and towards ridge 37C. Inner surface 47 may slidingly engage a forward surface 39 during this step. If clip 40 is urged far enough such that the edge 60 moves past apex 33B along forward surface 39B, clip 40 may then snap into engagement with second ridge 37B, as shown in FIG. 15C. It is important to note, however, that if force F is sufficient to move clip 40 in the direction of second ridge 37B, but insufficient to urge edge 60 past apex 33B, then clip 40 may subsequently compress due to the resiliency of the material of clip 40, and return to the position shown in FIG. 15A. It is also important to note that the clip 40 as shown in FIG. 15C may not return to ridge 37A absent surgeon intervention. Once clip 40 has moved to the location shown in FIG. 15C, it may not translate back to its positions in FIGS. 15A-15B without surgeon intervention.

In use with spinal applications involving adjacent vertebrae at a body site, a surgeon may first remove at least a portion of a intervertebral disc. A spacer or other material may be inserted between the vertebrae. The surgeon then may place the system 10 adjacent to the body site, such that a first carriage element 12A engages a first vertebrae and a second carriage element 12B engages a second vertebrae. At any time before or after the step of placing the system 10 adjacent to a body site, a surgeon may manually compress or expand the system 10 to decrease or increase its overall length. Once the system 10 is in position, the surgeon may fixedly attach the carriage elements 12A, 12B to their respective vertebrae by inserted bone fasteners (not shown) through fastener holes 14 and into the vertebrae. The surgeon may also manually compress or expand the system 10 intra-operatively at this point as well. The surgeon may then close the incision site.

Post-operatively, a carriage element 12 may translate relative to a plate 30 in response to forces applied on the system 10 in situ. For example, when using intervertebral material that resorps or otherwise reduces in size or strength after implantation into the body, vertebrae may tend to shift and/or drift closer to one another. The system 10 described herein is capable of responding to such forces by allowing carriage elements 12 to axially translate by allowing engaging clip 40 to engage subsequent ridges on a plate 30. The result may be that the system 10 is capable of compressing to a sufficient degree to respond to in situ, post-operative forces, and/or to maintain sufficient compression on intervertebral material to prevent expulsion and promote bone growth and/or fusion between vertebrae.

It is expressly contemplated that system 10 may be used in series or in combination with other devices. It is further contemplated that system 10 may be used with two, three or more vertebrae, either consecutive or non-consecutively. Other variations on the system, such as the relative size of the plate, carriage elements, and other components, will be appreciated by those skilled in the art.

While the previously-described method and advantages are described in reference to spinal application, it is also expressly contemplated that the system 10 described herein may be used with other parts of the body, such as joints, and long bone fractures. Further surgical uses will be appreciated by those skilled in the art.

It will be appreciated that engaging clip 40 may be constructed of a material that will allow the prongs 42, 44 to be separated in response to an applied force, but will also be resilient so as to return to their original configuration when the force is removed. A an example of a suitable material for engaging clip 40 is elgiloy. Captive clips 15 may be formed of the same material.

Each of the fasteners, plates, carriage elements, and other components disclosed herein may be formed of a titanium alloy such as titanium-aluminum-niobium, which may be anodized. One material for use with each of the plates and fasteners described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges broken to a maximum of 0.1 mm.

Figure 16:
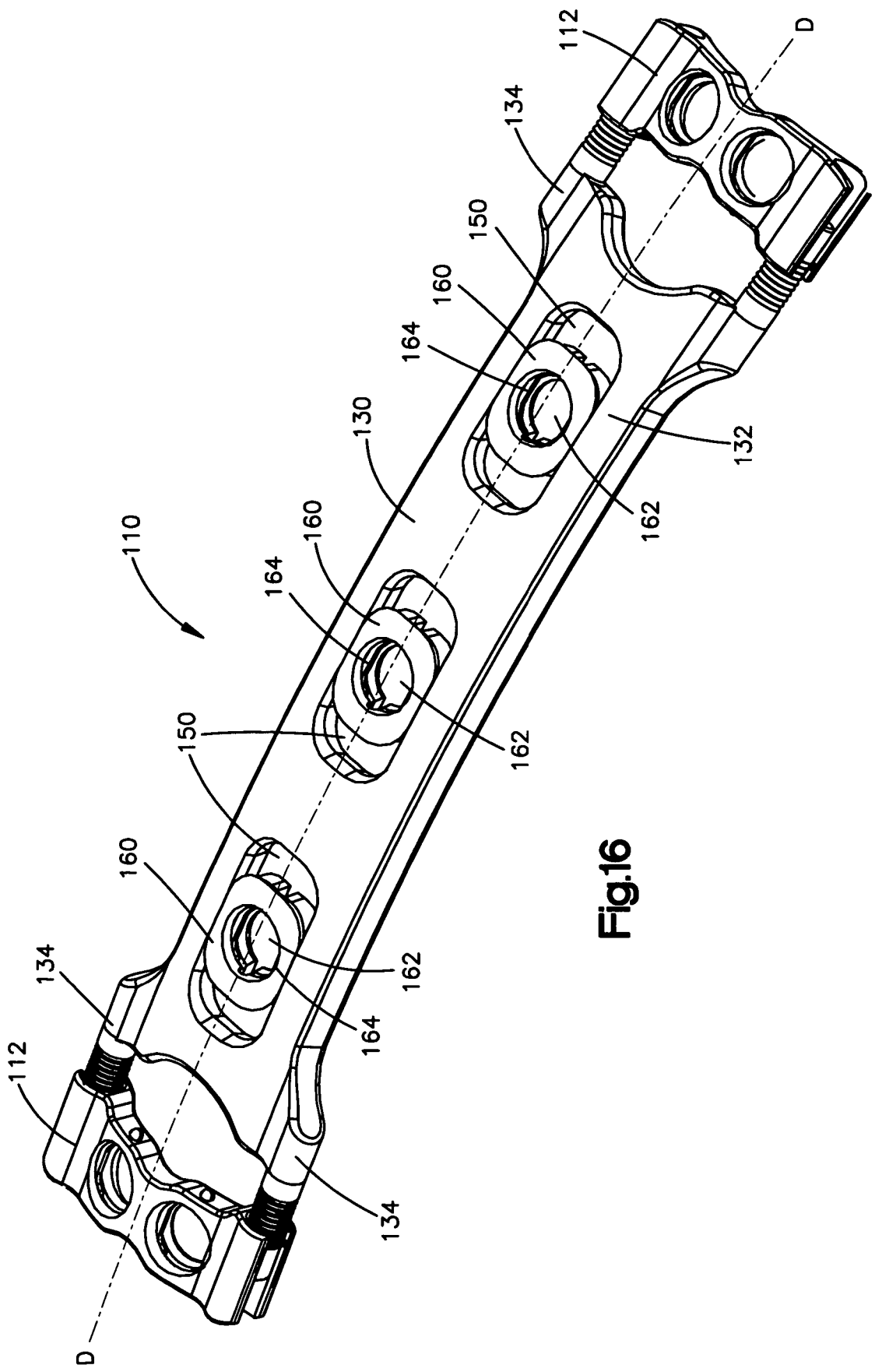
FIG. 16 is a perspective view of an alternative embodiment of the fixation system of the present invention.

FIG. 16 is a perspective view of an alternative embodiment 110 of a fixation system having longitudinal axis D-D. Carriage elements 112 may be substantially similar to carriage elements 12, as previously described in relation to FIGS. 1-15C. In this embodiment, plate 130 may include axially extending arms 134 having engaging portion 136 substantially similar to engaging portions 36 of arms 34. An engaging clip 40 may also be disposed within the channels 116 of the carriage elements 112. A significant difference between the embodiment shown in FIG. 16 and the previous embodiments is that body portion 132, rather than being in the form of an I-shaped bar, is in the form of an elongated plate configured to conform to a body surface. Body portion 132 may be provided with at least one window 150, with three such windows 150 shown in the embodiment of FIG. 16. Each window 150 may be provided with an intermediate carriage block 160 that can slide longitudinally within window 150. Each carriage block 160 may have a fastener hole 162, with a captive clip 164 disposed therein for engaging at least a portion of a bone fastener (not shown). Contacting surfaces between the window 150 and the carriage block 160 are dovetailed to prevent the carriage 160 from coming loose once it is assembled in window 150. The embodiment shown in FIG. 16 may achieve the translatable fixation of more than two consecutive vertebrae along a spinal column. Further details, materials, and methods of intermediate carriage element, and multi-level fixation, are described in U.S. patent application Ser. No. 10/932,392 entitled "Track-Plate Carriage System", by Suh et al., filed Sep. 2, 2004, the entire disclosure of which application is expressly incorporated by reference herein.

It should be noted that the aforementioned descriptions and illustrations have been provided as examples of the configurations of translation plates that may be designed and assembled using the principles of the invention. These examples will be understood to one of ordinary skill in the art as being non-limiting in that a fixation system employing one or more of the disclosed features may be produced as desired or required for a particular patient's need. Thus, the features disclosed are "modular" in nature.

This written description sets forth the best mode of the claimed invention, and describes the claimed invention to enable a person of ordinary skill in the art to make and use it, by presenting examples of the elements recited in the claims. The patentable scope of the invention is defined by the claims themselves, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and scope hereof.

What is claimed is:

1. A fixation system having a longitudinal axis, the fixation system comprising:
    a first carriage element capable of receiving one or more bone fasteners, the first carriage element having a first channel with at least one securing element disposed therein, and a second channel with at least one securing element disposed therein, wherein the first channel and second channel are formed on opposite sides of the longitudinal axis;

a second carriage element capable of receiving one or more bone fasteners, the second carriage element having a third channel with at least one securing element disposed therein and a fourth channel with at least one securing element disposed therein wherein the third channel and fourth channel are formed on opposite sides of the longitudinal axis; and a first plate having a body portion, a first arm a second arm, a third arm and a fourth arm wherein the first arm and third arm extend substantially transverse from the body portion on one side of the longitudinal axis and the second arm and the fourth arm extend substantially transverse from the body portion on the opposite side of the longitudinal axis and wherein the first arm has a first engaging portion having a series of ridges configured to engage the at least one securing element of the first channel, the second arm has a second engaging portion having a series of ridges configured to engage the at least one securing element of the second channel, the third arm has a third engaging portion having a series of ridges configured to engage the at least one securing element of the third channel and the fourth arm has a fourth engaging portion having a series of ridges configured to engage the at least one securing element of the fourth channel;

wherein each of the securing elements includes an engaging clip that comprises two arcuate prongs and a retaining element wherein at least a portion of the arcuate prongs engage a groove formed in the respective channel; and wherein the first and second carriage elements are configured to axially translate in only one direction relative to the first plate.

2. The fixation system of claim 1 wherein the first and second carriage elements are allowed to translate in situ.

3. The fixation system of claim 1, wherein the first carriage element is configured to be associated with a first bone segment, and the second carriage element is configured to be associated with a second bone segment.

4. The fixation system of claim 3, wherein the first and second bone segments are adjacent vertebrae.

5. The fixation system of claim 1, wherein the securing elements are configured to expand and retract during translation.

6. The fixation system of claim 1, wherein the ridges are configured to provide progressive resistance.

7. The fixation system of claim 1, wherein the first and second carriage elements have at least one fastener hole for receiving a bone fastener.

8. The fixation system of claim 1, wherein the first plate and first and second carriage element are curved to accommodate a desired body site.

* * * * *